(12) United States Patent
Mayoral et al.

(10) Patent No.: US 6,394,983 B1
(45) Date of Patent: *May 28, 2002

(54) CAP AND LUER CONNECTOR FOR A FLUID TRANSFER DEVICE

(75) Inventors: Joaquin Mayoral, Downers Grove, IL (US); Douglas L. Marriott, South Lebanon, OH (US); Richard W. Grabenkort, Barrington, IL (US)

(73) Assignee: Abbott Laboratories, Abbott Park, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/181,240

(22) Filed: Oct. 28, 1998
(Under 37 CFR 1.47)

(51) Int. Cl.[7] .................................................. A61M 5/32
(52) U.S. Cl. .......................... 604/192; 604/533; 604/905
(58) Field of Search ................................. 604/192, 905, 604/187, 198, 533

(56) References Cited

U.S. PATENT DOCUMENTS

| | | | |
|---|---|---|---|
| 3,950,917 A | 4/1976 | Choksi et al. | |
| 3,974,008 A | 8/1976 | Choksi | |
| 3,989,044 A | * 11/1976 | Meierhoefer | ................ 604/192 |
| 4,040,421 A | * 8/1977 | Young | ........................ 604/192 |
| 4,043,334 A | 8/1977 | Brown et al. | |
| 4,571,242 A | 2/1986 | Klein et al. | |
| 4,653,643 A | 3/1987 | Black | |
| 4,703,610 A | 11/1987 | Bach | |
| 4,724,973 A | 2/1988 | Shah | |
| 5,135,496 A | 8/1992 | Vetter et al. | |
| 5,624,402 A | * 4/1997 | Imbert | ........................ 604/111 |
| 5,807,345 A | * 9/1998 | Grabenkort | .................. 604/199 |
| 5,836,919 A | * 11/1998 | Skurka et al. | ............... 604/187 |
| 6,039,302 A | * 3/2000 | Cote, Sr. et al. | ......... 251/149.1 |

FOREIGN PATENT DOCUMENTS

| | | |
|---|---|---|
| DE | 29505787 | 6/1995 |
| EP | 0235870 | 9/1987 |
| EP | 0441171 | 8/1991 |

* cited by examiner

Primary Examiner—Angela D. Sykes
Assistant Examiner—Jeremy Thissell
(74) Attorney, Agent, or Firm—Beth A. Vrioni

(57) ABSTRACT

A cap and Luer connector arrangement with an improved external seal is provided for a fluid transfer connector or fitting that has a nozzle with a surrounding annular collar located coaxially within a surrounding sealing lip. The cap includes a structure of resilient material which defines an end wall, an annular, inner sleeve extending from the end wall, and an annular, outer skirt extending from the end wall to define an annular receiving channel between the outer skirt and the inner sleeve. At least a portion of the inner sleeve has an inner surface for sealingly engaging the nozzle. A distal end of the outer skirt includes a seal region having a V-shaped cross-sectional crevice. The Luer connector sealing lip and seal region are distorted when the sealing lip is received into the crevice during initial screwed-on installation of the cap to the Luer connector, forming an external seal. The sealing lip and seal region are heat set during autoclave-sterilization of the cap and Luer connector arrangement, which prevents reinstallation of the cap once removed.

21 Claims, 7 Drawing Sheets

CAP AND LUER CONNECTOR FOR A FLUID TRANSFER DEVICE

TECHNICAL FIELD

The present invention relates to a system for covering a portion of a fitting or connector on a medical device or other apparatus through which fluid is transferred. The present invention is especially suitable as a cap and male Luer lock connector combination for a Luer lock type of fluid transfer device such as a hypodermic syringe.

BACKGROUND OF THE INVENTION

One conventional type of syringe is a disposable syringe which is typically manufactured from inexpensive thermoplastic material, such as polyethylene or the like. Such syringes may have a standard end fitting for releasably receiving a hub from which a hollow, metal needle projects. In particular, such syringes typically have a 6% Luer taper conical nozzle fitting with a surrounding annular collar that has a double-start, right-hand, internal thread as shown in FIG. 1 of Part 2 of the International Standard ISO 594-2 (First Edition, 1991 05-01, Reference No. ISO 594-2: 1991 (E)) as published by the International Organization for Standardization, Case postale 56, CH-1211 Genèva 20, Switzerland.

The needle to be attached to the syringe end fitting projects from a molded hub having a pair of laterally extending lugs which are adapted to threadingly engage the double-start thread in the fitting collar. The molded hub defines a tapered female configuration for receiving the tapered conical nozzle of the syringe fitting as the hub is screwed into the syringe collar. Such an assembly has long been widely used.

The syringe may be prefilled. The prefilled syringe barrel is typically distributed without the needle attached, but with a cap or cover over the projecting nozzle.

It is, of course, desirable to provide such a prefilled syringe to the ultimate user with the fluid product contained in the syringe in a sterile condition. It is also desirable to ensure that the syringe nozzle is maintained in a sterile condition prior to attachment of the hub-mounted, hollow needle to the syringe nozzle.

While various syringe cap or cover designs are in use or have been proposed, it is difficult to provide a cap that maintains sterility of the syringe nozzle and surrounding collar structure in various applications and under a variety of circumstances. It would be advantageous to provide an improved cap which would maintain sterility of the threaded space within the annular collar surrounding the conical nozzle in addition to maintaining the sterility of the nozzle itself.

Some drugs, particularly protein based drugs, are advantageously stored in silicone-free containers. It would be beneficial if such an improved cap could accomplish a sealing function without the need for silicone lubricating/sealing oil. It would be beneficial for such an improved cap to have a lower potential for extractables. It would be beneficial for such an improved cap to be amenable to recycling.

Further, it would be beneficial if such an improved cap would evidence a prior removal, i.e., provide tamper evidence, after sterilization.

It would be advantageous to provide an improved cap for not only syringes but for other Luer connections as well.

In addition, it would be desirable to provide an improved cap which would provide improved sealing features without requiring more difficult or complicated installation and/or removal procedures.

Such an improved cap should also preferably accommodate manufacture from a relatively inexpensive material with relatively inexpensive manufacturing techniques so that the cap can be a low-cost, disposable item.

The present invention provides an improved cap which can accommodate designs having the above-discussed benefits and features.

SUMMARY OF THE INVENTION

A heat-set, tamper-evident seal arrangement of the present invention includes a first part, such as a cap, having an annular open sealing channel and a second part, such as a syringe or fitting, having a sealing lip surrounding a tapered annular surface. When the first and second parts are engaged together to form a seal, an inside leg of the open sealing channel is deflected outwardly by the tapered inside annular surface, and the sealing lip is deflected inwardly by an outside leg of the open channel. The sealing lip thereby axially overlies a portion of the inside leg.

The first and second part are subjected to high temperatures during a heat sterilizing procedure. The deflected or deformed sealing lip and the inside leg of the sealing channel are "heat-set" into their bent or stretched shapes. That is, the plastic material of the sealing lip and the inside leg of the sealing channel is subjected to a sufficiently high temperature to eliminate the residual resilient bending stress caused by the installation of the first part to the second part, i.e., the parts are stress relieved. The deflected or deformed sealing lip and the inside leg of the sealing channels assume a relaxed condition. After being heat-set by sterilizing, the first part can be removed from the second part only by resilient deflection of the heat-set deformed sealing lip and inside leg. However, after removal, the sealing lip and inside leg return to their deformed positions. At their deformed positions, the sealing lip and the inside leg of the open sealing channel mutually interfere to prevent reinstallation of the first part to the second part. Thus, a tamper evidence function and a reuse prevention function are provided.

A cap and male Luer fitting or connector according to a preferred embodiment of the present invention includes a cap having a skirt with a V-shaped annular sealing channel at a distal end thereof open toward the male Luer fitting. The male Luer fitting includes a sealing lip which is sized to be captured and deflected inwardly within the annular sealing channel as the cap is screwed tightly onto the connector. An inside annular leg, or cap seal ring, of the V-shaped annular sealing channel is deflected outwardly.

By heat sterilizing the tightly assembled cap and male Luer fitting, the sealing lip and V-shaped annular sealing channel are heat-set in their deflected postures. A portion of the sealing lip overlies the cap sealing ring in an axial direction. After removal of the cap, the heat-set deflected posture of the sealing lip and V-shaped annular channel have portions which mutually interfere in an axial installation direction to prevent reinstallation of the cap onto the male Luer fitting.

A cap of the present invention may be employed on any type of device having a fluid transfer connector. The cap is particularly useful for sealing a connector that has a nozzle with a surrounding annular collar. The cap is especially suitable for a 6% Luer tapered conical nozzle fitting with a surrounding annular collar that has a generally cylindrical exterior surface of a predetermined outer diameter and that has a double-start, right-hand, internal thread.

It is presently contemplated that a preferred, commercial embodiment of the cap of the present invention will be intended for use on a conventional male Luer lock syringe fitting. Also, the cap can be used for Luer access vials, sets, etc.; irrigation bottles; or ports on flexible bags.

The cap comprises a structure of resilient material. In a preferred embodiment, the cap is molded as a unitary structure from a plastic material. The structure of the cap may be characterized as having three basic portions: (a) an end wall, (b) an annular, inner sleeve with a male thread form, the sleeve extending from the end wall, and (c) an annular, outer skirt extending from the end wall. An annular receiving channel is defined between the outer skirt and inner sleeve.

The inner sleeve male thread form is for engaging the surrounding annular collar internal thread of the male Luer connector. The outer skirt includes the open V-shaped cross-section annular channel at its free edge opposite the end wall.

The male Luer connector, as a separate piece connector, includes an annular flange coaxially surrounding the annular collar. Extending from the annular flange, coaxially around the collar, is the sealing lip. The sealing lip is arranged to interfit within a crevice formed by a V-shaped cross-section annular sealing channel as the male Luer connector and cap are engaged. The collar internal thread engages the male thread form of the annular inner sleeve of the cap. The connector has a tapered annular surface which stretches and deforms the cap seal ring outwardly, which in turn bends the engaging sealing lip inwardly. During heat sterilization, the cap seal ring and the sealing lip are heat-set into this deformed and axially overlapping condition. After separation of the cap from the male Luer connector, the deformed sealing lip and cap seal ring axially interfere which prevents reinstallation of the same cap (or a new cap) to the male Luer connector.

At least a portion of the inner sleeve of the cap has an inner surface for sealingly engaging the nozzle of the connector. In a preferred embodiment, the cap inner sleeve has an inner surface which provides an annular gap around an outer surface of the nozzle. The nozzle is sealed closed at its open end against the end wall of the cap.

The cap can be cost effectively manufactured and easily installed. The cap seals without the use of silicone. The cap and connector fitting can be easily recycled.

Numerous other advantages and features of the present invention will become readily apparent from the following detailed description of the invention, from the claims, and from the accompanying drawings.

DESCRIPTION OF THE PREFERRED EMBODIMENT

While this invention is susceptible of embodiment in many different forms, this specification and the accompanying drawings disclose only one specific form as an example of the invention. The invention is not intended to be limited to the embodiment so described, however. The scope of the invention is pointed out in the appended claims.

For ease of description, the cap of this invention is described in one relative position, and terms such as upper, lower, horizontal, etc., are used with reference to this position. It will be understood, however, that the cap of this invention may be manufactured, stored, transported, used, and sold in an orientation other than the position described.

Figure 1:
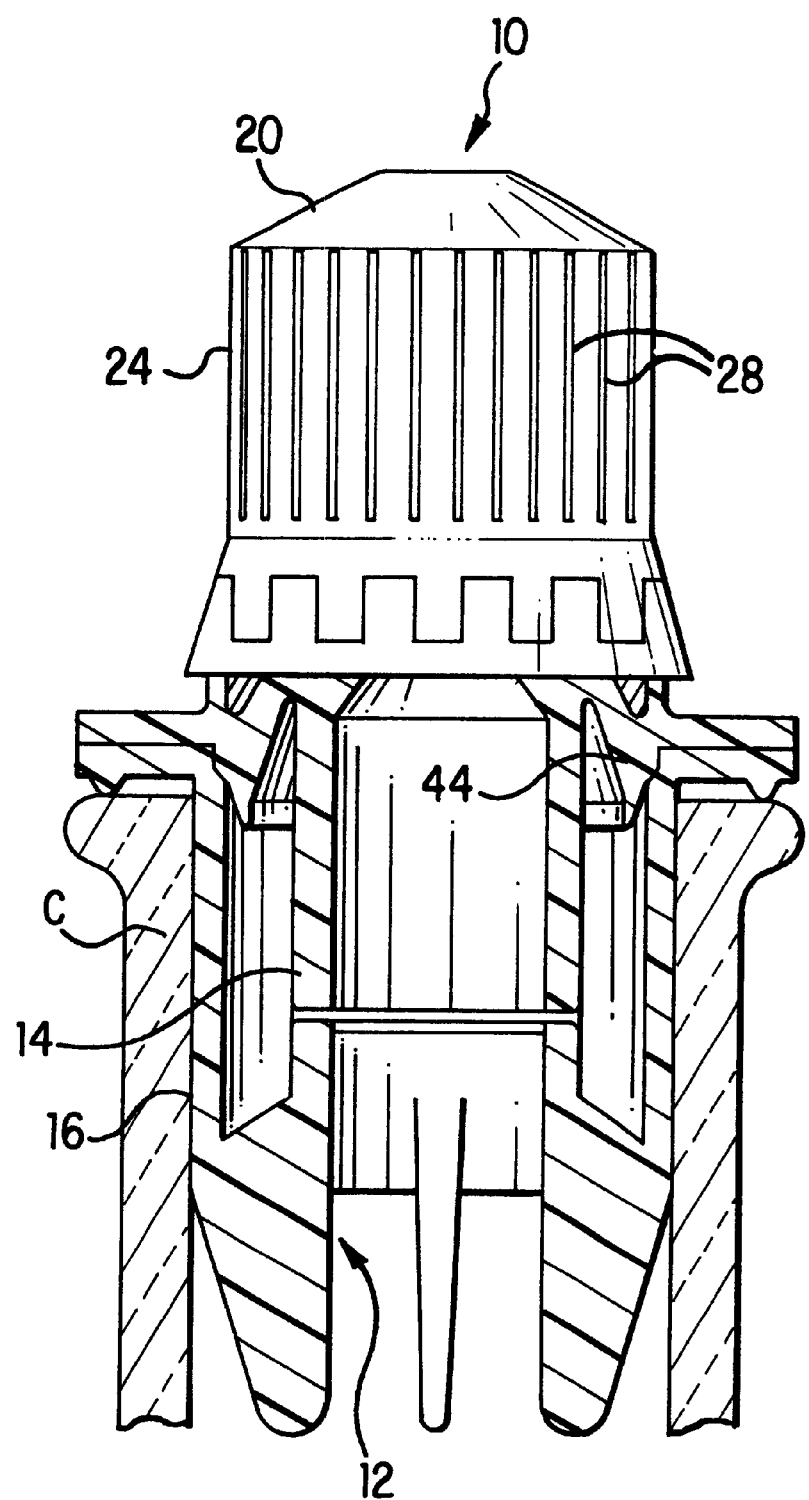
FIG. 1 is an elevational view, shown partly in cross-section, of the present invention showing a cap installed onto a container closure.

FIG. 1 illustrates a preferred embodiment of a cap 10 of the present invention screwed onto a container closure 12. The cap is shown in elevational view and the container closure in sectional view. Although the cap 10 is illustrated covering the container closure 12 in FIG. 1, the cap can also be used to close connectors on syringes, Luer access vials or sets, irrigation bottles, ports on flexible bags, or on any fluid container having a compatible connection, such as a Luer connection.

The closure 12 is engaged with a container C to be sealed thereto. The closure 12 includes a closure top portion or Luer connector or fitting 14 and a closure bottom portion or base 16.

The cap includes a domed top wall 20 and a depending skirt 24. On an outside of the depending skirt 24 are arranged a plurality of ribs 28 extending parallel to an axis of the skirt and providing a frictional gripping surface for removing and installing the cap 10. The ribs 28 extend in a spaced apart fashion around an outer circumference of the skirt 24.

Figure 2:
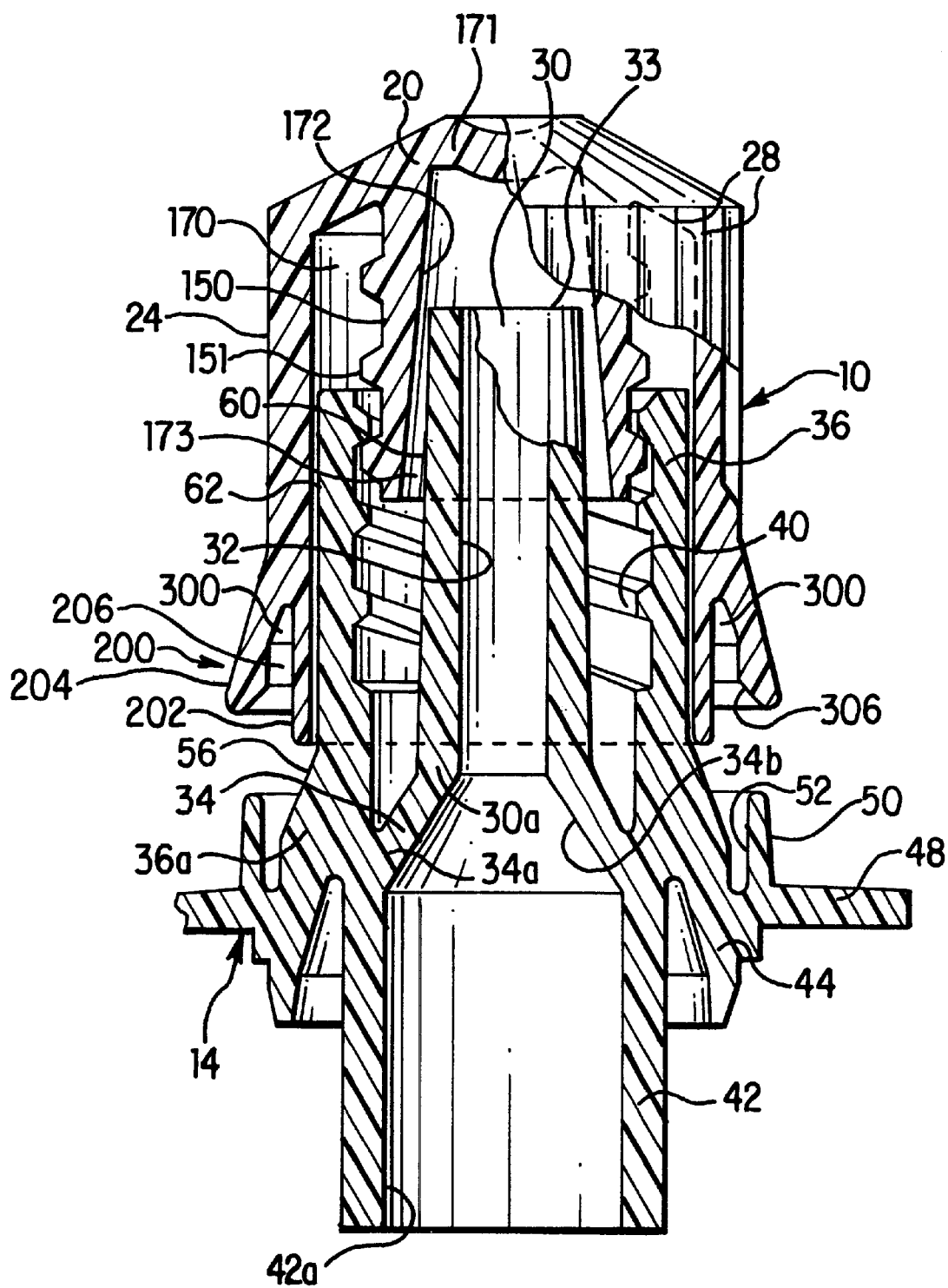
FIG. 2 is an elevational view, shown substantially in longitudinal cross-section, of a male Luer connector of the container closure and a cap of the present invention during installation of the cap on the male Luer connector.

FIG. 2 illustrates the cap 10 and top portion 14 of the closure 12 shown is FIG. 1. The top portion 14 may also be referred to as a "Luer fitting" or as a "Luer connector." The top portion 14 as illustrated is a unitary, molded piece and includes a male Luer nozzle 30 having an internal bore 32 open at a distal end 33 and connected at a base end 30a to a transition section 34. The transition section 34 is connected at a base end 34a thereof to a base end 36a of a male Luer connector collar 36. The collar has a double-start, right hand internal thread form 40 arranged on an inside surface thereof The collar 36 surrounds the nozzle 30. The transition section 34 includes a bore 34b open to the bore 32 of the nozzle 30. An open delivery sleeve 42 in flow communication with the container C is connected to the transition section 34 at the base end 34a thereof and has a central bore 42a open to the bore 34b of the transition section 34.

Extending downwardly from the base end 36a of the collar 36 is a surrounding base seal ring 44, which also surrounds the sleeve 42 and is used to seal the top portion 14 to the bottom or base part 16, of the container closure 12.

Extending outwardly from the base end 36a of the collar 36 is an annular flange 48 used for mounting the top portion 14 to the bottom portion 16. Extending up from the annular flange 48 is a sealing lip 50 which is spaced from and surrounds the base part 36a of the collar 36. A socket 52 is formed between the sealing lip 50 and the base part 36a. A tapered annular surface 56 on the base part 36a extends partly into the socket 52.

Although a Luer fitting 14 embodied in a separate-piece container closure 12 is shown as an example, the Luer fitting 14 can instead be formed as a unitary portion of the container. In the case of a syringe, the Luer fitting can be integrated with the syringe barrel at one end thereof In that case, the base part 16, the outwardly extending flange 48, the base seal ring 44, and the sleeve 42 can be eliminated. The sealing lip 50, the collar 36, and the nozzle 30 would all extend coaxially from the end of the syringe barrel, to be engaged by the cap as described below.

The nozzle 30 and the collar 36 can be shaped and sized in accordance with International Standard ISO 594-2 First Edition 1991-05-01 Reference Number ISO 594-2:1991(E), entitled "Conical fittings with a 6% (luer) taper for syringes, needles and certain other medical equipment-Part 2: Lock fittings" and/or ANSI/HIMA MD70.1-1983 (Revision of ANSI 270.1-1955), entitled: "American National Standard for Medical Material-Luer Taper Fittings-Performance."

The nozzle 30 has an exterior, frustoconical surface 60 which may be characterized as defining a 6% conical taper on the diameter. That is, there is a 0.060 inch/inch taper on the diameter. This can be calculated by measuring the exterior diameter at a first location along the length of the nozzle and by measuring a second exterior diameter at a second location along the length of the nozzle 30. The difference between the two diameters is divided by the distance between the locations of the two diameters, and the result is multiplied by 100 to yield the percent conical taper.

The collar 36 has a generally cylindrical, exterior surface 62 which carries the double-start, right hand internal thread form 40. The collar 36 is shorter than the nozzle 30 so that the distal end of the nozzle 30 extends outwardly beyond the distal end of the collar 36.

The double-start, internal thread form 40 has a steeply pitched, spiral configuration and is adapted to threadably engage the four corners of a square flange provided on a hub (not illustrated) of a hypodermic needle. The needle hub is typically molded from thermo plastic material, and the hub defines a female recess having a 6% Luer conical taper for receiving and engaging the syringe nozzle 30 in a sealing relationship. The internal thread form 40 can also engage a Luer connector having a full male Luer thread on an outside of a female Luer nozzle.

The cap 10 of the present invention may be advantageously employed to maintain a sterile, sealed condition of the Luer nozzle 30 and of the thread space defined within the outer Luer connector collar 36. A preferred embodiment of the cap 10 is molded as a unitary structure from a plastic material, such as polypropylene.

The cap 10 includes an end wall 20 and an annular, inner sleeve 150 extending from the end wall 20. The annular outer skirt 24 extends from the end wall 20 to define an annular receiving channel 170 between the outer skirt 24 and the inner sleeve 150. The inner sleeve 150 has male threads 151 for engaging the connector collar internal thread form 40.

As illustrated in FIG. 2, the cap 10 includes a short, central projection 171 extending from the end wall 20 within the cap inner sleeve 150. This projection can be sized and adapted to seal against the open end 33 of the nozzle 30 when the cap is fully engaged.

The inner sleeve 150 has a tapered inner surface 172 which is sized to provide an annular gap 173 between the outer surface 60 of the nozzle 30 and the inner surface 172 throughout its length. This gap 173 insures that the cap projection 171 will be completely engaged with the open end 33, without interference between the adjacent surfaces 60, 172.

In particular, FIG. 2 illustrates the as-molded configuration of the resilient cap prior to installation. The outer skirt 24 of the cap 10 includes a V-shaped cross-sectional sealing channel 200 at a distal end thereof from the end wall 20. The sealing channel 200 is defined by an inner cap seal ring 202 and an outer lock ring 204. Between the inner cap seal ring 202 and the outer lock ring 204, the sealing channel provides an annular crevice 206 which is configured to receive the sealing lip 50 of the Luer connector top part 14. The lock ring 204 is shorter, thicker and more rigid than the cap sealing ring 202, and the sealing lip 50.

Figure 3:
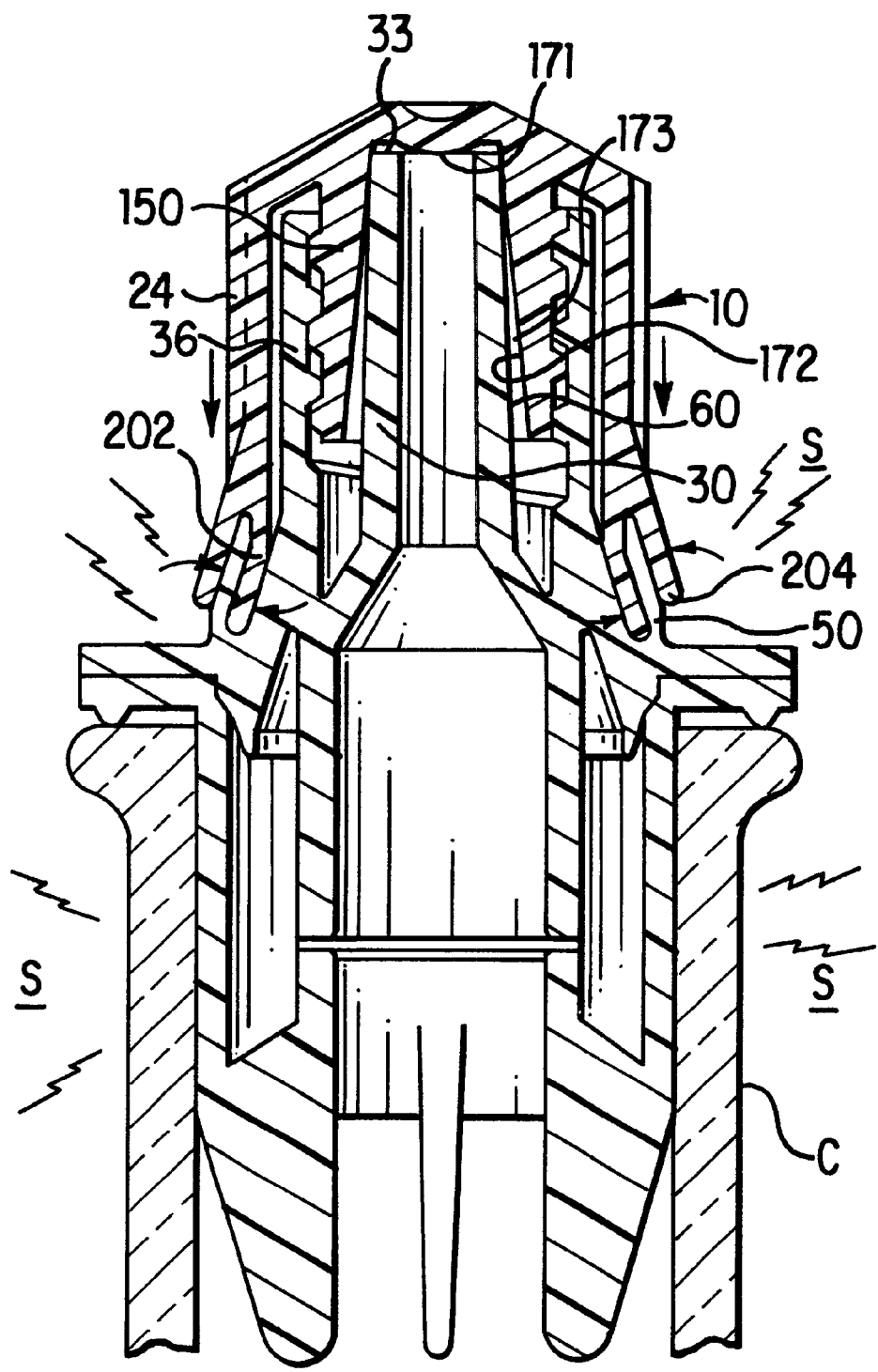
FIG. 3 is a longitudinal cross-sectional view of the cap and closure of FIG. 1 with the cap completely engaged to the male Luer connector.
Figure 3A:
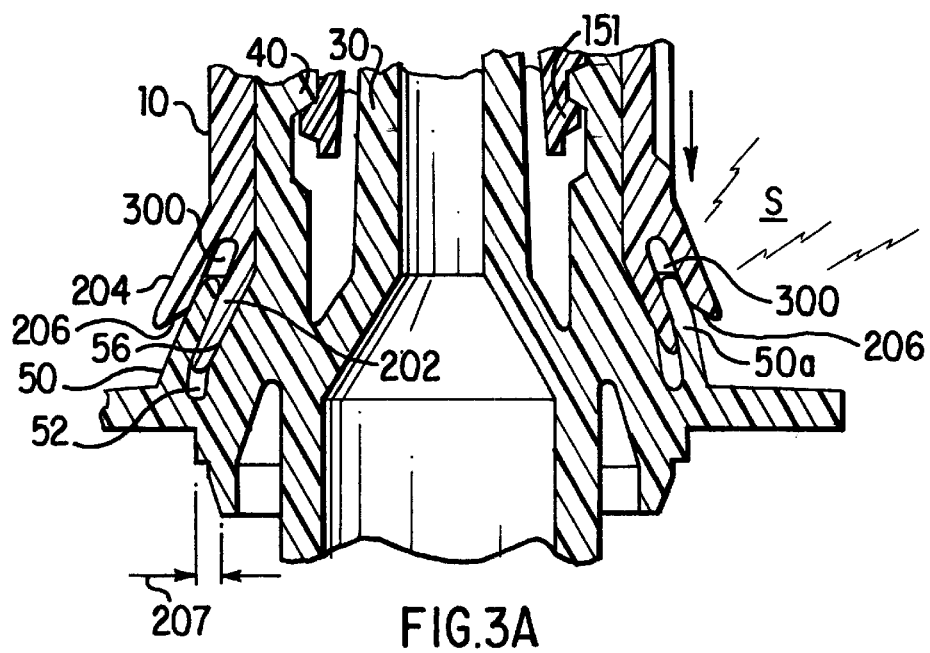
FIG. 3A is an enlarged, fragmentary cross-sectional view of the connector and the cap of FIG. 3.

As shown in FIGS. 3 and 3A, the diameter of the cap seal ring 202 is such that during installation of the cap 10 to the connector 14, the inner cap seal ring 202 is stretched open by sliding on the tapered surface 56 of the more rigid annular collar 36. The cap seal ring 202 is thus received into the socket 52 on the Luer connector 14 while the sealing lip 50 is received into the annular crevice 206 of the cap 10. The lock ring 204 assumes a position outside of the sealing lip 50 of the Luer connector 14, pressing inwardly against a top portion 50a of the lip 50.

FIGS. 3 and 3A illustrate the cap 10 completely installed on the fitting 14. The female thread form 40 is tightly engaged with the male thread form 151 of the cap. The V-shaped sealing channel 200 is completely engaged with the cap seal ring 202 having been deformed outwardly by the tapered surface 56 to be fit within the socket 52.

The sealing lip 50 has been deformed inwardly by coaction of the lock ring 204 and the crevice 206 and the outward deflection of the cap seal ring 202 by the inclined surface 56. The sealing lip 50 thus overlies, in an axial direction, the cap seal ring 202 by a distance 207.

In this position, the entire assembly is "autoclaved" or heat sterilized by a surrounding heat source such as steam. During this heat treatment, the original stress field generated by the deformation is relaxed away and new contact pressure is created when the assembly is cooled, leaving the seal permanently locked. Thus, the cap seal ring 202, the sealing lip 50, and the lock ring 204 are heat set in their bent configuration (shown in FIG. 3). As a result of this design configuration, a leak tight seal is thus effected (maintained throughout the entire sterilization process), which also seals the thread space to prevent external contamination.

Figure 4:
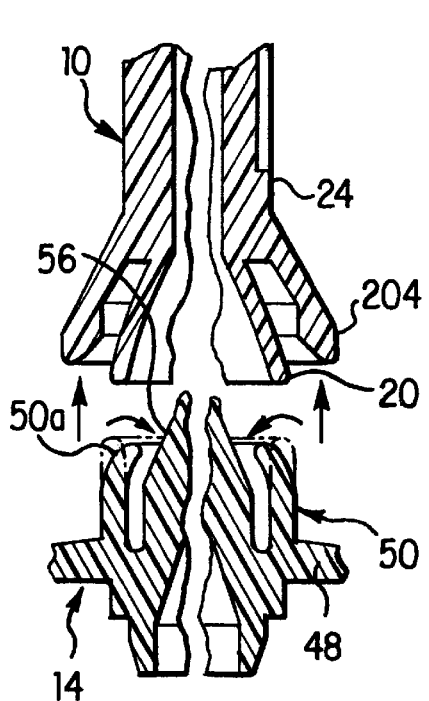
FIG. 4 is a cross-sectional, fragmentary view of the fitting and cap of FIG. 3 after the cap has been removed from the connector.

If the cap 10 is then unscrewed from the connector 14, as shown in FIG. 4, the mutual engagement of the sealing lip 50, cap seal ring 202, and the lock ring 204 is resiliently released, i.e., the somewhat bent postures of the two annular parts 202, 204 are straightened to be mutually disengaged.

Figure 5:
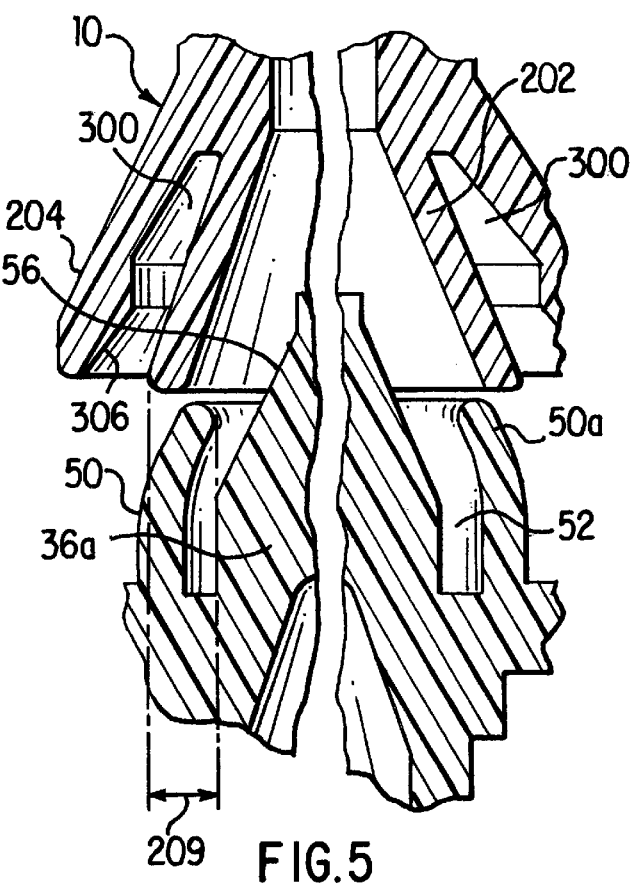
FIG. 5 is an enlarged cross-sectional, fragmentary view of the connector and the cap of FIG. 4 shown during an attempted reinstallation.
Figure 6:
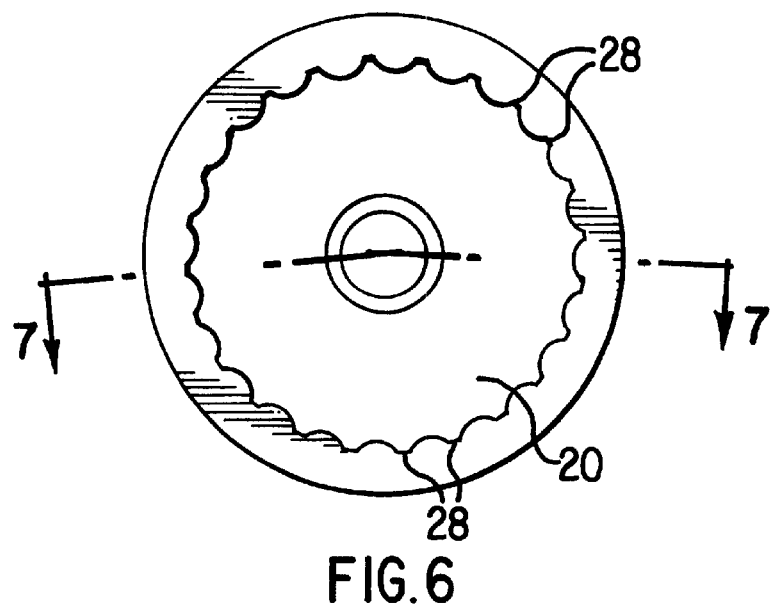
FIG. 6 is a top plan view of the cap shown in FIG. 2.

As shown in FIG. 4 when the cap 10 is removed from the fitting part 14 the bent annular sealing lip 50 deflects outwardly to allow passage of the bent cap seal ring 202 (shown in phantom) but then springs back inwardly to its heat set position as illustrated in FIGS. 3, 3A and 5.

After separation, the sealing lip 50 and cap seal ring 202 resume their heat-set posture. Because of the deformed condition of the sealing lip 50 and the cap seal ring 202, the cap cannot thereafter be threaded back onto the connector 14 due to interference between the cap seal ring 202 and the sealing lip 50, by an amount 209 in an axial direction, approximately equivalent to the distance 207 as illustrated in FIG. 5. The cap seal ring 202 which has been deflected outwardly and heat set compared to its position shown in FIG. 2, interferes with the heat-set bent sealing lip 50 to prevent the cap seal ring 202 from entering the socket 52 which prevents further engagement between the two parts. Thus, after heat setting, the cap can be removed but not reinstalled.

This design is effective to prevent removal of the cap from the fitting, subsequent contamination, and unauthorized reclosing of the cap to the fitting. It also serves as a tamper evident feature which gives evidence of the prior removal of the cap 10 from the connector 12.

Figure 7:
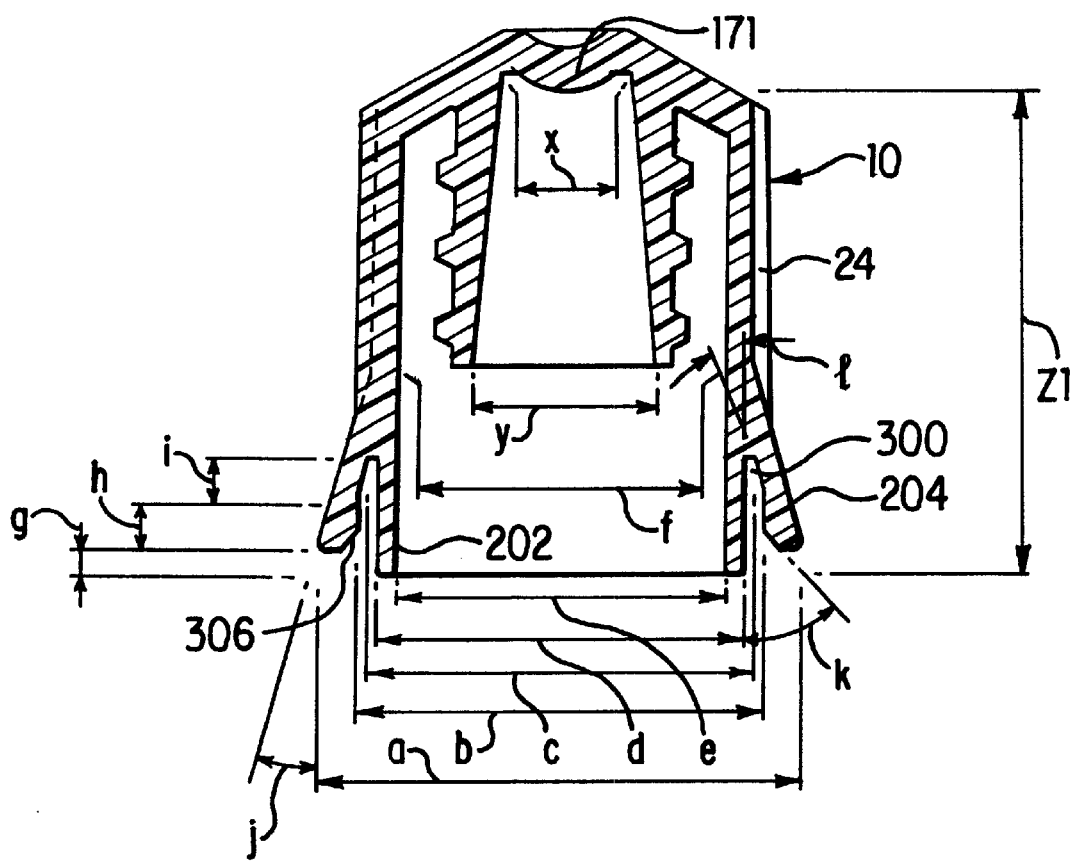
FIG. 7 is a cross-sectional view of the cap taken through plane 7—7 of FIG. 6.
Figure 8:
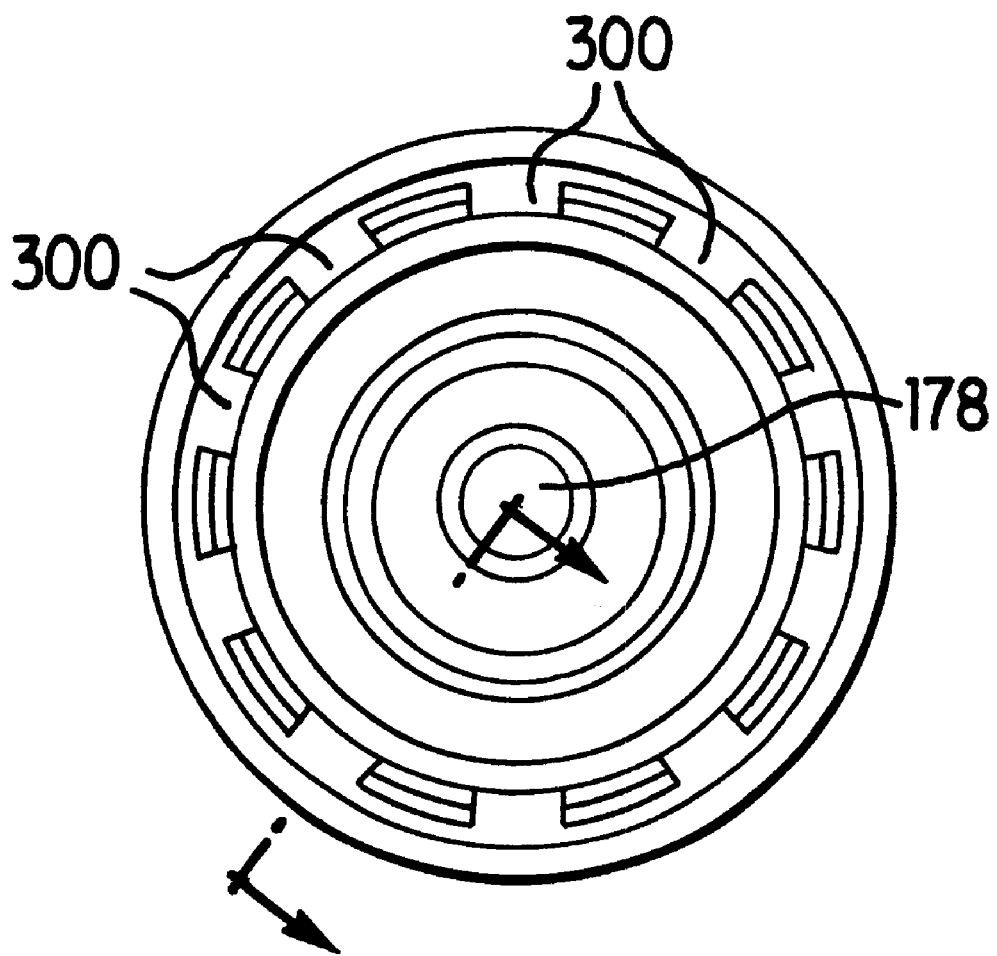
FIG. 8 is a bottom view of the cap shown in FIG. 7.

FIGS. 7 and 8 illustrate the cap in detail. Within the open crevice 206 of the cap 10 are located substantially wedge shaped reinforcing blocks 300 spaced apart around a circumference of the skirt 24. The blocks 300 add stiffness to the lock ring 204, and maintain correct spacing between the lock ring 204 and the cap seal ring 206.

The cap seal ring 202 has an inside diameter e sized such that the cap seal ring 202 will land on the tapered surface 56 to be guided and stretched thereby into the socket 52. The lock ring 204 also has an annular bevel 306 for guiding the sealing lip 50 of the connector 14 into the crevice 206.

Also shown in FIG. 7 is the inwardly directed protrusion 171 for sealing the open end 34 of the nozzle 30 when the nozzle is fully engaged with the cap 10. The protrusion 171 has a convex, domed shape for reliably sealing the circular open end 33 of the nozzle 30. Thus, in addition to the exterior seal formed by the annular parts 50, 202, 204 and 56, an effective inner seal is also provided when the cap end wall 20 engages the distal end 33 of the nozzle 30 when the cap 10 is completely installed onto the Luer fitting 14.

Figure 9:
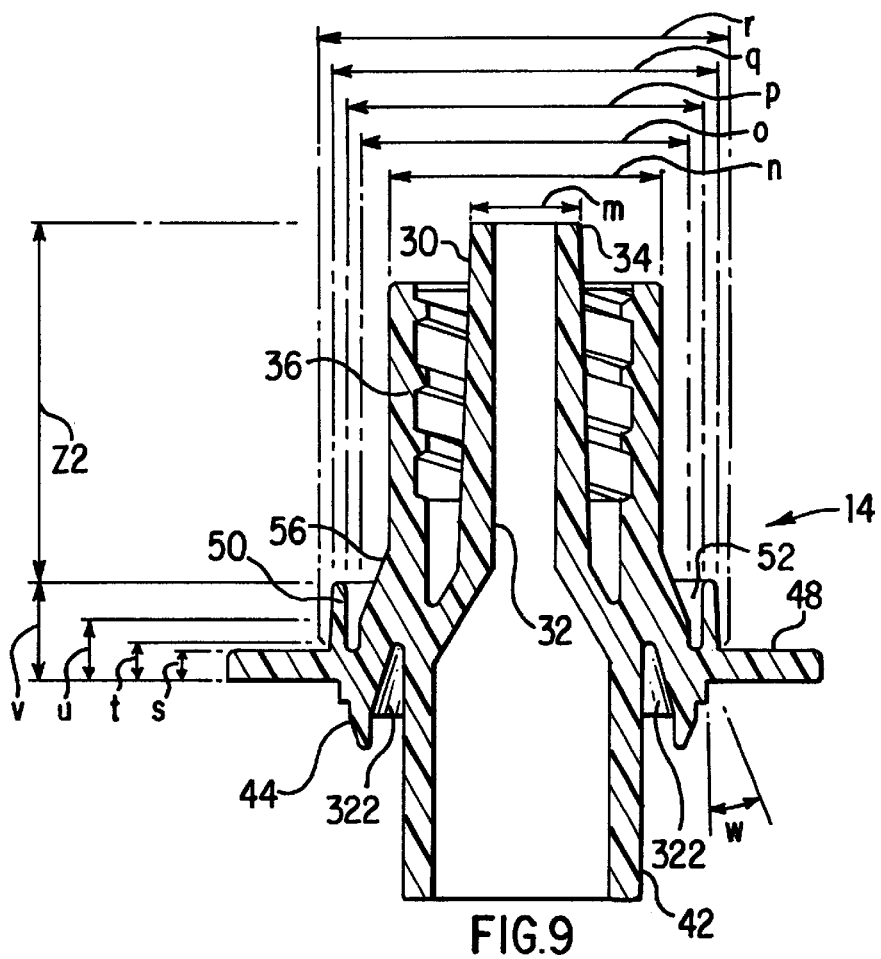
FIG. 9 is a cross-sectional view of the male Luer lock connector shown in FIG. 2.

FIG. 9 illustrates the male Luer fitting 14 in more detail including the relative optimal dimensions of the inclined surface 56, the socket 52, and the sealing lip 50.

Figure 10:
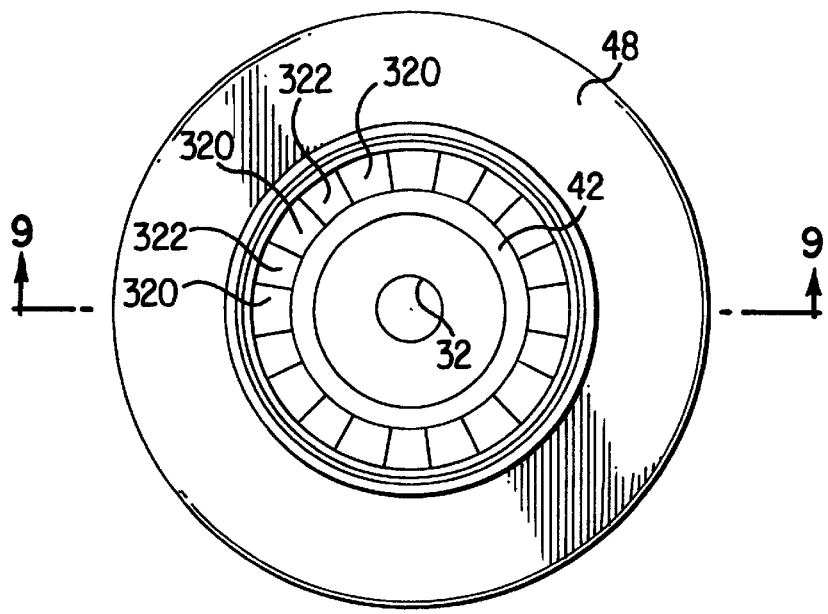
FIG. 10 is a bottom view of the male Luer lock connector shown in FIG. 9.

FIG. 10 also illustrates that the fitting 14 includes a plurality of spaced apart tool slots 320 around an underside of the base region of the transition section 34. The tool slots 320 are separated by posts 322 which allow for tool engagement of the molded fitting 14 to screw the threaded fitting from the mold during manufacture.

The embodiment of the present invention is advantageously configured with precise dimensions and angularities to achieve the external seal and the internal seal between the cap and the fitting or connector.

Table 1 lists the presently preferred dimensions for various features of the fitting 14, and the corresponding cap 10.

| Dimension Designation | Dimension (Inches) or Angle (Degrees) |
| --- | --- |
| a | .582 |
| b | .494 |
| c | .470 |
| d | .444 |
| e | .408 |
| f | .400 |
| g | .034 |
| h | .056 |
| i | .060 |
| j | 15° |

-continued

| Dimension Designation | Dimension (Inches) or Angle (Degrees) |
| --- | --- |
| k | 40° |
| l | 15° |
| m | .156 |
| n | .390 |
| o | .465 |
| p | .510 |
| q | .546 |
| r | .555 |
| s | .041 |
| t | .055 |
| u | .089 |
| v | .145 |
| w | 20° |
| x | .160 |
| y | .225 |
| z1 | .617 |
| z2 | .530 |

The cap and closure or Luer fitting of the invention are preferably composed of PP9544 injection mold grade polypropylene or PP9122 blow mold grade polypropylene.

Although the cap 10 is ideally suited for sealing the dispensing end of a Luer lock fitting for a syringe or other container, it will be appreciated that the cap may be employed to seal any fluid transfer connector that has the same type of tapered conical nozzle fitting with a surrounding annular collar. Such fluid transfer connectors may be found on various medical devices, such as fluid transfer tube administration sets, medical equipment, containers, ampules and vials, etc.

Additionally, although the cap and fitting combination described above is intended to be used with standard Luer lock fittings, the invention is not limited to such fittings and can be adapted in principle to nonstandard fittings or connectors as well.

Also, it is encompassed by the present invention that the relative engaging and sealing elements of the cap and fitting can be reversed. That is, the open sealing channel 200 can be provided on the fitting, connector or closure part 14 and the sealing lip 50 and tapered surface 56 can be provided on the cap 10.

It will be readily apparent from the foregoing detailed description of the invention and from the illustrations thereof that numerous variations and modifications may be effected without departing from the true spirit and scope of the novel concepts or principles of this invention.

What is claimed is:

1. A cap and fluid fitting combination for a fluid transfer device, comprising:

a fluid fitting including a fluid port, an annular sealing lip surrounding said fluid port, and an annular wall located radially between said sealing lip and said fluid port, said annular wall and said sealing lip form a socket therebetween; and a cap engaged to said fluid fitting and adapted for closing said fluid port, said cap having a ring adapted to seal against said sealing lip, said cap having a depending skirt including said cap seal ring and a lock ring which together define a channel with a crevice for receiving said sealing lip, said socket.

2. The combination of claim 1 wherein said fluid port includes an open distal end and a base end with a bore extending between said open distal end and said base end, said annular wall is tapered and is angled inwardly from said base end toward said distal end.

3. The combination of claim 2 wherein said cap seal ring being deflected outwardly by said tapered annular wall to enter said socket and said sealing lip being deflected inwardly to overlie a portion of said cap seal ring.

4. A cap and fluid fitting for a fluid transfer device, comprising:
a fluid fitting including:
a fluid nozzle having an axis, an open distal end and a base end with a central bore extending between said open distal end to said base end;
an annular sealing lip extending proximate said base end in a direction parallel to said axis of said nozzle, said annular sealing lip surrounding said nozzle; and
a tapered annular wall located radially between said sealing lip and said nozzle, where said tapered annular wall is angled inwardly in a direction from said base end towards said distal end and said tapered annular wall and said sealing lip form a socket therebetween; and
a cap having an end wall and a depending skirt, where a free edge of said skirt defines a cap seal ring and a lock ring which together define a substantially V-shaped cross-section annular sealing channel having a crevice, where said cap is positionable over said nozzle with said crevice receiving said sealing lip, said cap seal ring is deflected outwardly by said tapered annular wall to enter said socket, and said sealing lip is deflected inwardly to overlie a portion of said cap seal ring.

5. The cap and fitting combination according to claim 4 further comprising an annular collar connected to, and surrounding said nozzle, where said annular collar extends from said tapered annular wall and has an inside thread form on an inside surface thereof; and
said cap includes an inside sleeve having an outside thread form for engagement with said inside thread form of said annular collar, where when said cap turns, said outside thread form engages said inside thread form to progress said cap onto said fluid fitting.

6. The cap and fitting combination according to claim 5 wherein said inside sleeve includes an inside annular surface sized to receive said nozzle without interference therebetween when said cap is screwed onto said fluid fitting.

7. The cap and nozzle combination according to claim 4 wherein when said cap is advanced completely onto said fitting, said open distal end of said nozzle is seated against said end wall of said cap.

8. The cap and fitting combination according to claim 4 wherein said skirt includes a plurality of reinforcing wedge shaped blocks that are spaced apart circumferentially around said skirt and located within said crevice and connect said lock ring and said cap seal ring.

9. The cap and fitting combination according to claim 4 when said cap further comprises a plurality of axial ribs around an outside surface of said skirt to provide a friction grip for unscrewing the cap from the nozzle.

10. A cap and fluid fitting combination for a fluid transfer device, comprising:
a fluid fitting having a fluid port and an annular sealing lip surrounding said fluid port; and
a cap engaged to said fluid fitting having:
a body adapted for closing said fluid port, said body having a cap seal ring adapted to seal against said sealing lip; and
a lock portion which surrounds said sealing lip and bends said sealing lip at least partially over said cap seal ring.

11. The combination according to claim 10 wherein said fitting further comprises a tapered annular wall surrounding said fluid port and located radially between said annular sealing lip and said fluid port, where said tapered annular wall is arranged to deflect said cap seal ring outwardly and said lock portion is arranged to deflect said sealing lip inwardly.

12. The combination according to claim 11 wherein said cap and said fitting include mutually engaging thread formations for advancing said cap onto said fitting.

13. The combination according to claim 10 wherein said cap seal ring and said sealing lip are heat-set after said cap is engaged to said fluid fitting.

14. A cap and Luer connector combination for a fluid transfer connector comprising:
a Luer connector including a base end and a conically-shaped nozzle having a first open distal end, and a surrounding annular collar having a generally cylindrical exterior surface with a second open distal end and having an internal thread, and a sealing lip having a third open distal end and surrounding said annular collar, said annular collar having a tapered wall portion facing said sealing lip, and said nozzle, said collar and said sealing lip arranged coaxially extending from said base end to said first, second and third open distal ends respectively; and
a cap having a unitary, molded structure defining an end wall, an annular, inner sleeve extending from said end wall, and an annular, outer skirt extending from said end wall to define an annular receiving channel between said outer skirt and said inner sleeve, at least an end portion of said outer skirt having an open annular crevice located between an inside portion and an outside portion of said end portion which receives said sealing lip when the cap is installed onto said Luer connector, said tapered wall portion deflecting said inside portion of said end portion outwardly and said sealing lip inwardly, such that said sealing lip at least partially overlaps said inside portion in an axial direction.

15. The cap and Luer connector combination according to claim 14 wherein said inside portion comprises an annular cap seal ring and said outside portion comprises an outer annular lock ring where said lock ring is substantially more rigid than said cap seal ring and said seal ring extends to a distal end further than a distal end of said lock ring.

16. The cap and Luer connector combination according to claim 14 wherein said open annular crevice is substantially V-shaped and said cap further comprising a plurality of wedge shaped blocks spaced around the circumference of said skirt and located within said V-shaped crevice but recessed from an outer surface of said V-shaped crevice to allow entry of said sealing lip into said V-shaped crevice.

17. The cap and Luer connector combination according to claim 14 wherein said cap is sized such that when said cap is completely engaged to said fitting, said open end of said nozzle is sealed closed by said end wall of said cap.

18. A cap and fluid connector combination, comprising:
a fluid connector having a base portion, a nozzle having an open end and extending from said base portion, and a sealing lip surrounding said nozzle and also extending from said base portion; and a cap having an end wall and an outer skirt extending from said end wall, at least a portion of a distal end of said outer skirt from said end wall having a crevice for receiving and bending said sealing lip when the cap is installed onto said fluid connector, said sealing lip bent to be axially overlying a part of said portion.

19. The combination according to claim 18 wherein said sealing lip is heat-set after installation of said cap.

20. The combination according to claim 19 wherein said sealing lip is composed of polypropylene.

21. The combination according to claim 19 wherein said cap is sized with respect to said fluid connector such that when said fluid connector and said cap are completely engaged, said open end of said nozzle is sealed closed by said end wall.

* * * * *